Dec. 21, 1965 D. L. ARMSTRONG ET AL. Plant Pat. 2,580
NECTARINE PLANT
Filed June 1, 1964
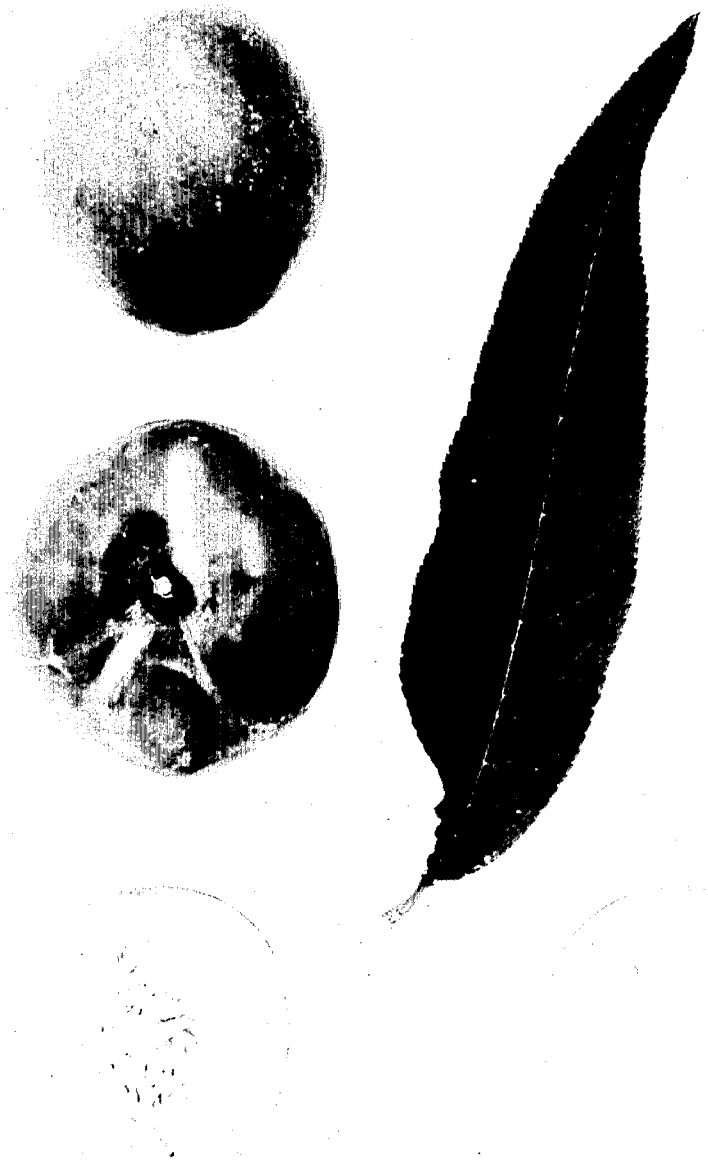
Inventors.
D. L. Armstrong and
H. C. Sevin
By: Robb & Robb
Attorneys.

United States Patent Office

Plant Pat. 2,580

Patented Dec. 21, 1965

2,580

NECTARINE PLANT

David L. Armstrong and Herbert C. Swim, Ontario, Calif., assignors to Armstrong Nurseries, Inc., Ontario, Calif., a corporation of California Filed June 1, 1964, Ser. No. 371,860
1 Claim. (Cl. Plt.—41)

The present invention relates to a new and distinct variety of nectarine tree which originated from open pollination of an unnnamed and unpatented nectarine variety. The parent variety originated from an extended series of crosses, which on one side goes back three generations to the ancestor varieties known as "Babcock" peach, "Boston" nectarine, "Gold Mine" nectarine, and "July Elberta" peach, all unpatented, and on the other side going back two generations to "Gold Mine" nectarine and "July Elberta" peach.

The general objectives achieved by our new nectarine variety were an early fruit ripening habit, with the fruit being of the yellow-fleshed type and of good quality. However, these objectives are combined with additional improved features which represent a unique and desirable combination which distinguishes the new variety from its parent, as well as from all others of which we are aware, as evidenced by the following features which are outstanding in the new variety:

(1) A vigorous tree habit, with a chilling requirement between that of "Robin" peach (Plant Patent No. 529) and that of "June Gold" peach (Plant Patent No. 1,884);

(2) Production of large fruit crops;

(3) A very early fruit-ripening habit, usually occurring several days later than "Robin" peach in southern California;

(4) Distinctive and attractively colored fruit when fully ripe, said fruit being heavily blushed with red over a yellow-green base color;

(5) A very attractive, uniform and nearly round fruit shape, with no beak and relatively insignificant and smooth suture lines;

(6) A characteristically smooth skin and lack of pubescence which differentiates the nectarine from the peach;

(7) Yellow fruit flesh, with no trace of red at the stone;

(8) An essentially free-stone habit when the fruit is fully ripe, despite a strong tendency of the flesh to initially adhere to the stone because of the early ripening habit; and (9) A particularly good quality and good flavor for a nectarine of the early-ripening class.

The unnamed parent variety was a yellow-fleshed, free-stone nectarine whose fruit ripens in the general period of "Redhaven" peach (unpatented), with the fruit being of medium size, nearly round in shape, and having an extensive and solid red skin color. The quality and flavor of the fruit of this parent were very good, and the tree was very productive, but had a medium chilling requirement.

In comparison with the antecedents of this nectarine variety, the new variety is distinguished from its immediate parent primarily by ripening of the fruit from two to three weeks earlier than the fruit of the parent; it is distinguished from the ancestor "Babcock" peach by being earlier ripening and yellow-fleshed, whereas the fruit of the "Babcock" peach ripens about a month later and is white-fleshed; it is distinguished from its ancestor "Boston" nectarine primarily by being earlier in its ripening habit, with the fruit having an extensive and solid red skin color, in contrast to the late mid-season ripening habit and considerably less red skin color of this "Boston" variety; in comparison with "Gold Mine" nectarine, the new variety is primarily distinguished by being yellow-fleshed and earlier ripening, whereas "Gold Mine" is white-fleshed and ripens in mid-season; and in comparison with the ancestor "July Elberta" peach, the new variety is primarily distinguished by having an earlier ripening habit and an extensive and solid red skin color of the fruit as contrasted with the fact that "July Elberta" is a peach which ripens about a month later and has relatively little skin color.

The only other nectarine variety which most nearly resembles our new nectarine variety is "Sunrise" nectarine (Plant Patent No. 1,256), but the new variety is definitely distinguished therefrom by the fact that its fruit ripens a few days earlier and has less skin speckling than the fruit of the variety "Sunrise."

Asexual reproduction of our new variety by budding, as performed by us at Wasco, California, shows that the foregoing characteristics and distinctions come true to form and are established and transmitted through succeeding propagations.

The accompanying drawing shows typical specimens of the fruit and foliage of our new nectarine variety, with both exterior and sectional views of the fruit being shown, the latter exposing the stone in one half-section and the cavity in the other half-section, with all of the views being depicted in color as nearly true as it is reasonably possible to make the same in a color illustration of this character.

The following is a detailed description of our new variety, as based upon observations of specimens grown at Wasco, California, with color terminology in accordance with Robert F. Wilson's Horticultural Color Chart (hereinafter abreviated as (W)) and Ridgway's Color Standards and Nomenclature (hereinafter abbreviated as (R)), except where general color terms of ordinary dictionary significance are obvious:

*Tree*

Habit: Vigorous; upright-spreading.

Chilling requirement: Medium; between that of "June Gold" peach and that of "Robin" peach.

Fruit production: It bears a heavy crop; considerable thinning is necessary.

Current growth:

*Surface texture.*—Smooth at first, with lenticels small and minute; with age some larger, cracked, slightly raised lenticels appear toward the base of the more vigorous shoots.

*Color.*—At first green, or reddish on exposed surfaces, with lenticels appearing as small, near white dots; all becoming more brown with age.

Two-year wood:

*Surface texture.*—Generally smooth, with slightly raised, irregular, longitudinal striations and numerous lenticels.

*Color.*—Brown.

Old wood:

*Surface texture.*—Generally smooth, with moderate number of large, raised lenticels, and some small longitudinal fissures.

*Color.*—From grey to greyish-brown or reddish brown on more exposed surfaces.

Leaves:

*Size.*—Length—from 5½ inches to 7 inches. Width—from 1¼ inches to 1½ inches.

*Shape.*—Lanceolate, with apex acuminate.

*Color (mature).*—Upper surface—near Cress Green, Plate XXXI (R). Under surface—near Light Elm Green, Plate XVII (R).

*Petiole.*—Medium length; from thick to medium thickness.

*Margin.*—Finely serrate; glandular.

*Glands.*—Mixed; reniform and globular; medium size; usually 2 or 3, but sometimes 4 or 5 in number; borne both on the petiole and on the base of the blade.

Vegetative buds:

*Size.*—Small.

*Shape.*—Ovoid, unless compressed between flower buds.

*Scales.*—Pubescence thick and moderate length.

*Color.*—Dark brown.

*Flowers*

Dates of first and full bloom: Over a five-year period of observation, varied from February 22 to March 7 for first bloom, and from March 3 to March 16 for full bloom, due to weather variations from year to year.

Dormant flower buds:

*Shape.*—Ovoid.

*Scales.*—Pubescent.

*Color.*—Dark brown, with pubescence giving a whitish effect.

Size: (when fully open): Showy; about 1½ inches in diameter.

Petalage: Single; usually 5 petals.

Form: Cupped.

Color (open flower): Between Rose Pink, Plate 427/3, page 126 (W) and Rose Pink, Plate 427/2, page 126 (W), darkening toward center with age to between Phlox Pink, Plate 625/2, page 77 (W) and Phlox Pink, Plate 625, page 77 (W).

*Fruit*

Ripening dates: Generally ripens in very late May to very early June at Wasco, California; over five years of observation the date of first ripening ranged from May 28 to June 4; ripens in the general period of several days after "Robin" peach.

Maturity when described: Eating ripe.

Size: From generally small to medium size.

*Axial diameter.*—From 2 to 2¼ inches.

*Transverse diameter in suture plane.*—From 2 to 2⅜ inches.

*Transverse diameter at right angles to suture plane.*—From 2 to 2⅜ inches.

For: Relatively uniform; globose; slightly compressed laterally.

Suture: Generally shallow; extending from base to apex; slight depression beyond pistil point.

Ventral surface: Rounded; sometimes slightly lipped toward apex; lips when present usually unequal.

Stem cavity: Usually rounded and slightly elongated in suture plane, with suture showing on one side.

*Depth.*—About ¼ inch.

*Width.*—From about ⅜ to ½ inch.

Base: From rounded to truncate.

Apex: Usually rounded; pistil point insignificant.

Stem: Medium caliper; glabrous; from medium to weak adherence to stone. Length—about ¼ inch.

Skin:

*Thickness.*—Thin.

*Texture.*—Medium.

*Tenacity to flesh.*—Free.

*Pubescence.*—None; characteristic smooth skin of the nectarine.

*Color.*—Ground color varies from near Uranium Green, Plate 63/1, page 63 (W) to near Straw Yellow, Plate 604, page 67 (W), heavily blushed with from near Brick Red, Plate 016, page 106 (W) to near Oxblood Red, Plate 00823/3, page 161 (W).

Flesh:

*Quality.*—Medium firm; melting; fine texture.

*Aroma.*—Pronounced.

*Flavor.*—Good balance between sugar and acid, with distinctive nectarine flavor.

*Color.*—Between Saffron Yellow, Plate 7/2, page 7 (W) and Sulphur Yellow, Plate 1/2, page 1 (W); surface of pit cavity between Lemon Yellow, Plate 4/2, page 4 (W) and Canary Yellow, Plate 2/2, page 2 (W).

Stone:

*Tenacity of flesh.*—Basically free, but because of early ripening, stone adheres to flesh along both dorsal and ventral edges until the fruit is fully ripe.

*Size.*—Medium; length from about 1 to 1¼ inches; width from about ⅞ to 1⅛ inches; thickness ⅝ to 1 inch.

*Form.*—Ovoid; cuneate toward apex.

*Base.*—Somewhat oblique.

*Hilum.*—Narrow.

*Apex.*—Acute.

*Sides.*—Slightly unequal; curved on right and left sides; irregularly furrowed toward apex; pitted toward base.

*Ventral edge.*—Medium thickness; generally without wing toward base.

*Dorsal edge.*—Narrow; with shallow narrow groove toward base; ridges on either side interrupted.

*Color.*—Between Light Vinaceous Cinnamon, Plate XXIX (R) and Cinnamon, Plate XXIX (R).

We claim:

A new and distinct variety of nectarine tree of the yellow-fleshed, free-stone, fruit-bearing type, substantially as herein shown and described, characterized particularly as to novelty by the unique combination of a vigorous tree habit, with a chilling requirement between that of "Robin" peach (Plant Patent No. 529) and that of "June Gold" peach (Plant Patent No. 1,884), production of large fruit crops, a very early fruit-ripening habit, usually occurring several days later than "Robin" peach in southern California, distinctive and attractive colored fruit when fully ripe, said fruit being heavily blushed with red over a yellow-green base color, a very attractive, uniform and nearly round fruit shape, with no beak and relatively insignificant and smooth suture lines, a characteristically smooth skin and lack of pubescence which differentiates the nectarine from the peach, yellow fruit flesh, with no trace of red at the stone, an essentially free-stone habit when the fruit is fully ripe, despite a strong tendency of the flesh to initially adhere to the stone because of the early ripening habit, and a particularly good quality and good flavor for a nectarine of the early-ripening class.

No references cited.

ABRAHAM G. STONE, *Primary Examiner.*